(12) United States Patent
Park et al.

(10) Patent No.: US 8,503,714 B2
(45) Date of Patent: Aug. 6, 2013

(54) DROPOUT CORRECTION IN ULTRASOUND STRAIN IMAGING

(75) Inventors: Sang Shik Park, Seoul (KR); Dong Kuk Shin, Seoul (KR); Dong Ki Ahn, Seoul (KR); Mok Kun Jeong, Seoul (KR)

(73) Assignee: Medison Co., Ltd., Kangwon-Do (KR)

( * ) Notice: Subject to any disclaimer, the term of this patent is extended or adjusted under 35 U.S.C. 154(b) by 161 days.

(21) Appl. No.: 13/107,356

(22) Filed: May 13, 2011

(65) Prior Publication Data

US 2012/0099757 A1   Apr. 26, 2012

(30) Foreign Application Priority Data

Oct. 21, 2010 (KR) .................. 10-2010-0102711

(51) Int. Cl.
*G06K 9/00* (2006.01)
(52) U.S. Cl.
USPC .......................................................... 382/100
(58) Field of Classification Search
None
See application file for complete search history.

(56) References Cited

U.S. PATENT DOCUMENTS

| | | | | |
|---|---|---|---|---|
| 4,463,380 A | * | 7/1984 | Hooks, Jr. ..................... | 348/580 |
| 6,508,768 B1 | * | 1/2003 | Hall et al. ..................... | 600/443 |
| 6,542,626 B1 | | 4/2003 | Brouwer et al. | |
| 6,894,702 B2 | * | 5/2005 | Stamm et al. ................. | 345/613 |
| 7,176,941 B2 | * | 2/2007 | Stamm et al. ................. | 345/613 |
| 2007/0032726 A1 | * | 2/2007 | Osaka et al. .................. | 600/459 |
| 2007/0234806 A1 | * | 10/2007 | Jiang et al. ..................... | 73/570 |

FOREIGN PATENT DOCUMENTS

KR  10-2001-00602 52  7/2001

OTHER PUBLICATIONS

Korean Office Action, issued in Korean Patent Application No. 10-2010-0102711, dated Oct. 31, 2011.

* cited by examiner

*Primary Examiner* — Nancy Bitar
(74) *Attorney, Agent, or Firm* — McDermott Will & Emery LLP

(57) ABSTRACT

Embodiments for correcting a dropout in a strain image in an ultrasound system are disclosed. In one embodiment, a processing unit sets a first window on each of pre-compression ultrasound frame data and post-compression second ultrasound frame data, move the first window in a predetermined direction and compute a correlation between the pre-compression ultrasound frame data and the post-compression ultrasound frame data within the first window to obtain a displacement corresponding to a value of each pixel of target ultrasound frame data. The processing unit sets one of pixels of the target ultrasound frame data as a reference pixel, sets a second window to encompass predetermined numbers of pixels positioned around the reference pixel, checks whether a displacement computation error corresponding to a dropout occur based on the pixel values within the second window and resets, when the dropout occurs, the value of the reference pixel.

13 Claims, 3 Drawing Sheets

FIG. 4

DROPOUT CORRECTION IN ULTRASOUND STRAIN IMAGING

CROSS-REFERENCE TO RELATED APPLICATIONS

The present application claims priority from Korean Patent Application No. 10-2010-0102711 filed on Oct. 21, 2010, the entire subject matter of which is incorporated herein by reference.

TECHNICAL FIELD

The present disclosure generally relates to strain imaging, and more particularly to dropout correction in strain imaging.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional images of internal features of an object (e.g., human organs).

Generally, the ultrasound image is displayed in a Brightness-mode (B-mode) by using reflectivity caused by an acoustic impedance difference between the tissues of the target object. However, if the reflectivity of the target object is hardly different from those of the neighboring tissues such as tumor, cancer or the like, then it is not easy to recognize the target object in the B-mode image.

To cope with the problem of recognizing the tumor, cancer and the like in the B-mode, an ultrasound elasticity imaging has been developed to visualize the mechanical characteristics of the tissues based on differences responsive to pre-compression and post-compression. Such imaging proved very helpful for diagnosing lesions such as tumor and cancer, which otherwise are hardly recognized in the B-mode image, in soft tissues (e.g., breast). The ultrasound elasticity imaging may utilize the scientific property that the elasticity of the tissues is related to a pathological phenomenon. For example, the tumor or cancer is relatively stiffer than the surrounding normal tissues. Thus, when stress is uniformly applied, a strain of the tumor or cancer may be typically smaller than those of the surrounding tissues. Strain is deformation of a target object due to stress applied per area and Young's modulus may be defined as a ratio of stress over strain. The strain is a differential value of a displacement. The displacement may indicate how much tissues in the target object are moved between pre-compression and post-compression.

The ultrasound system may set a window on each of pre-compression frame data and post-compression frame data and move the window in an axial direction for correlation operation therebetween, thereby obtaining displacements. In such a case, when a position gap between the windows set on the pre-compression frame data and the post-compression frame data is beyond a range of a phase, a decorrelation error may occur.

Conventionally, the ultrasound system is configured to determine an initial displacement from a current position of the window (i.e., displacement, which has already computed in an axial direction at a current position of the window) and move the window by the initial displacement to compute a displacement in order to remove the decorrelation error. In such a case, however, if an error in the initial displacement occurs, an error is maintained in an axial direction. Thus, a dropout, i.e., a horizontal line in a strain image may be generated.

SUMMARY

Embodiments for forming correcting a dropout in strain imaging in an ultrasound system are disclosed herein. In one embodiment, by way of non-limiting example, an ultrasound system comprises: an ultrasound data acquisition unit configured to acquire first ultrasound frame data where compression is not applied to a target object and second ultrasound frame data where compression is applied to the target object; and a processing unit configured to set a first window on each of the first ultrasound frame data and the second ultrasound frame data, move the first window in a predetermined direction and compute a correlation between the first ultrasound frame data and the second ultrasound frame data within the first window to obtain a displacement corresponding to a value of each pixel of third ultrasound frame data, the processing unit being further configured to set one of pixels of the third ultrasound frame data as a reference pixel, set a second window to encompass predetermined numbers of pixels positioned around the reference pixel, check whether a displacement computation error corresponding to a dropout occur based on the pixel values within the second window and reset, when the dropout occurs, the value of the reference pixel.

In another embodiment, a method of correcting a dropout of a strain image in an ultrasound system, comprises: a) acquiring first ultrasound frame data where compression is not applied to a target object; b) acquiring second ultrasound frame data where compression is applied to the target object; c) setting a first window on each of the first ultrasound frame data and the second ultrasound frame data; d) moving the first window in a predetermined direction and computing a correlation between the first ultrasound frame data and the second ultrasound frame data within the first window to obtain a displacement corresponding to a value of each pixel of third ultrasound frame data; e) setting one of pixels of the third ultrasound frame data as a reference pixel and setting a second window to encompass predetermined numbers of pixels positioned around the reference pixel; and f) checking whether a displacement computation error corresponding to a dropout occur based on the pixel values within the second window and resetting, when the dropout occurs, the value of the reference pixel.

In yet another embodiment, a computer-readable storage medium storing instructions that, when executed by a computer, cause the computer to perform a dropout correcting method comprises: a) setting a first window on each of first ultrasound frame data acquired while compression is not applied to a target object and the second ultrasound frame data acquired while compression is applied to the target object; b) moving the first window in a predetermined direction and computing a correlation between the first ultrasound frame data and the second ultrasound frame data within the first window to obtain a displacement corresponding to a value of each pixel of third ultrasound frame data; c) setting one of pixels of the third ultrasound frame data as a reference pixel and setting a second window to encompass predetermined numbers of pixels positioned around the reference pixel; and d) checking whether a displacement computation error corresponding to a dropout occur based on the pixel values within the second window and resetting, when the dropout occurs, the value of the reference pixel.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIG. 4 is a schematic diagram showing an example of setting a window.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
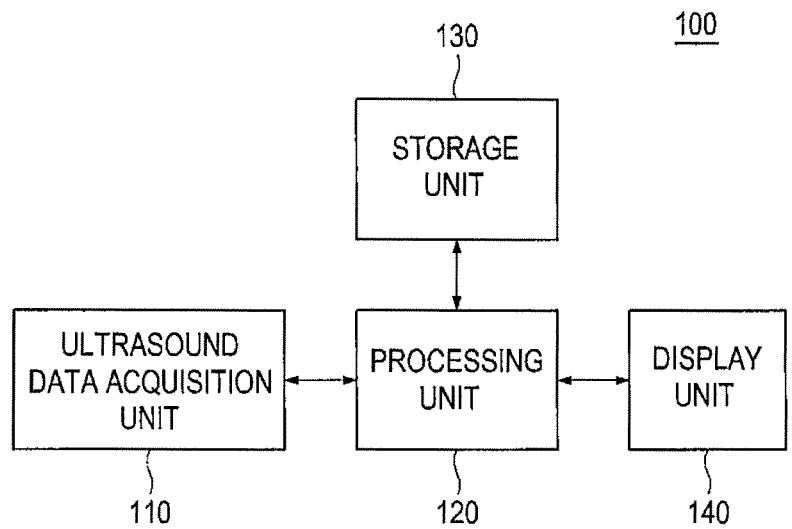
FIG. 1 is a block diagram showing an illustrative embodiment of an ultrasound system.

Referring to FIG. 1, an ultrasound system constructed in accordance with one embodiment is shown. The ultrasound system 100 may include an ultrasound data acquisition unit 110, a processing unit 120, a storage unit 130 and a display unit 140.

The ultrasound data acquisition unit 110 may be configured to transmit ultrasound beams to a target object and receive ultrasound echoes reflected from the target object to thereby form ultrasound data representative of the target object. An operation of the ultrasound acquisition unit will be described in detail by referring to FIG. 2.

Figure 2:
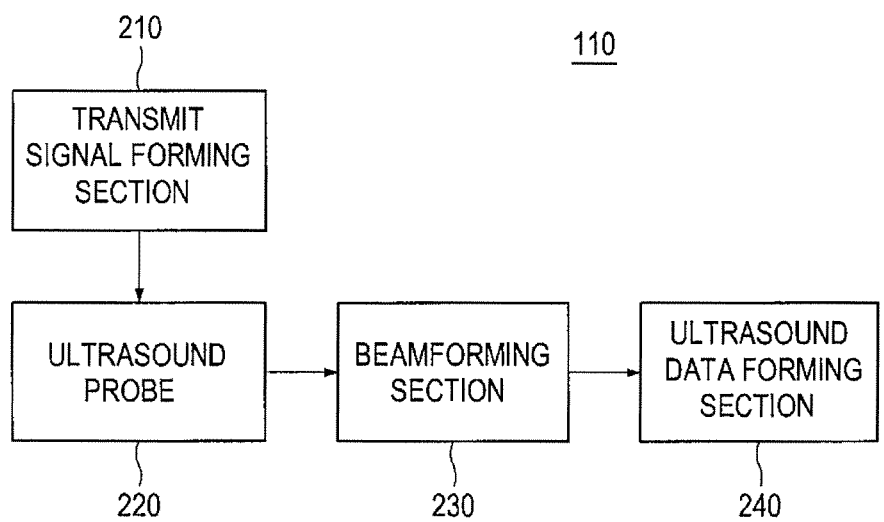
FIG. 2 is a block diagram showing an illustrative embodiment of an ultrasound data acquisition unit of FIG. 1.

FIG. 2 is a block diagram showing an illustrative embodiment of the ultrasound data acquisition unit 110. Referring to FIG. 2, the ultrasound data acquisition unit 110 may include a transmit signal forming section 210. The transmit signal forming section 210 may generate a plurality of transmit signals and apply delays to the transmit signals.

The ultrasound data acquisition unit 110 may further include an ultrasound probe 220, which is coupled to the transmit signal forming section 210. The ultrasound probe 220 may include an array transducer containing a plurality of transducer elements for reciprocal conversion between electric signals and ultrasound signals. The ultrasound probe 220 may be configured to transmit ultrasound signals in response to the transmit signals. The ultrasound probe 220 may be further configured to receive ultrasound echoes reflected from the target object to thereby output receive signals. In one embodiment, the receive signals may include first receive signals obtained without applying compression to the target object and second receive signals obtained with applying compression to the target object. The compression may be applied by using the ultrasound probe 220. In such a case, a compression plate may be mounted around a front side of the ultrasound probe 220. In another embodiment, an additional device for compressing the target object may be employed.

The ultrasound data acquisition unit 110 may further include a beam forming section 230, which is coupled to the ultrasound probe 220. The beam forming section 230 may be configured to digitize the electrical receive signals into digital signals. The beam forming section 230 may also apply delays to the digital signals in consideration of distances between the elements of the ultrasound probe 220 and focal points. The beam forming section 230 may further sum the delayed digital signals to form receive-focused signals. In one embodiment, the beam forming section 230 may form first receive-focused signals based on the first receive signals and second receive-focused signals based on the second receive signals.

The ultrasound data acquisition unit 110 may further include an ultrasound data forming section 240, which is coupled to the beam forming section 230. The ultrasound data forming section 240 may be configured to form ultrasound frame data sets corresponding to a plurality of frames based on the receive-focused signals. The ultrasound frame data sets may include RF data sets or in-phase/quadrature (IQ) data sets. However, the ultrasound data may not be limited thereto. The ultrasound data forming section 240 may be further configured to perform a variety of signal processing (e.g., gain adjustment, filtering, etc.) upon the receive-focused signals. In one embodiment, the ultrasound data may include a first ultrasound frame data set formed based on the first receive-focused signals and a second ultrasound frame data set formed based on the second receive-focused signals.

Referring back to FIG. 1, the processing unit 120, which is coupled to the ultrasound data acquisition unit 110, may be embodied with at least one of a central processing unit, a microprocessor, a graphic processing unit and the like. However, the processing unit 120 may not be limited thereto.

Figure 3:
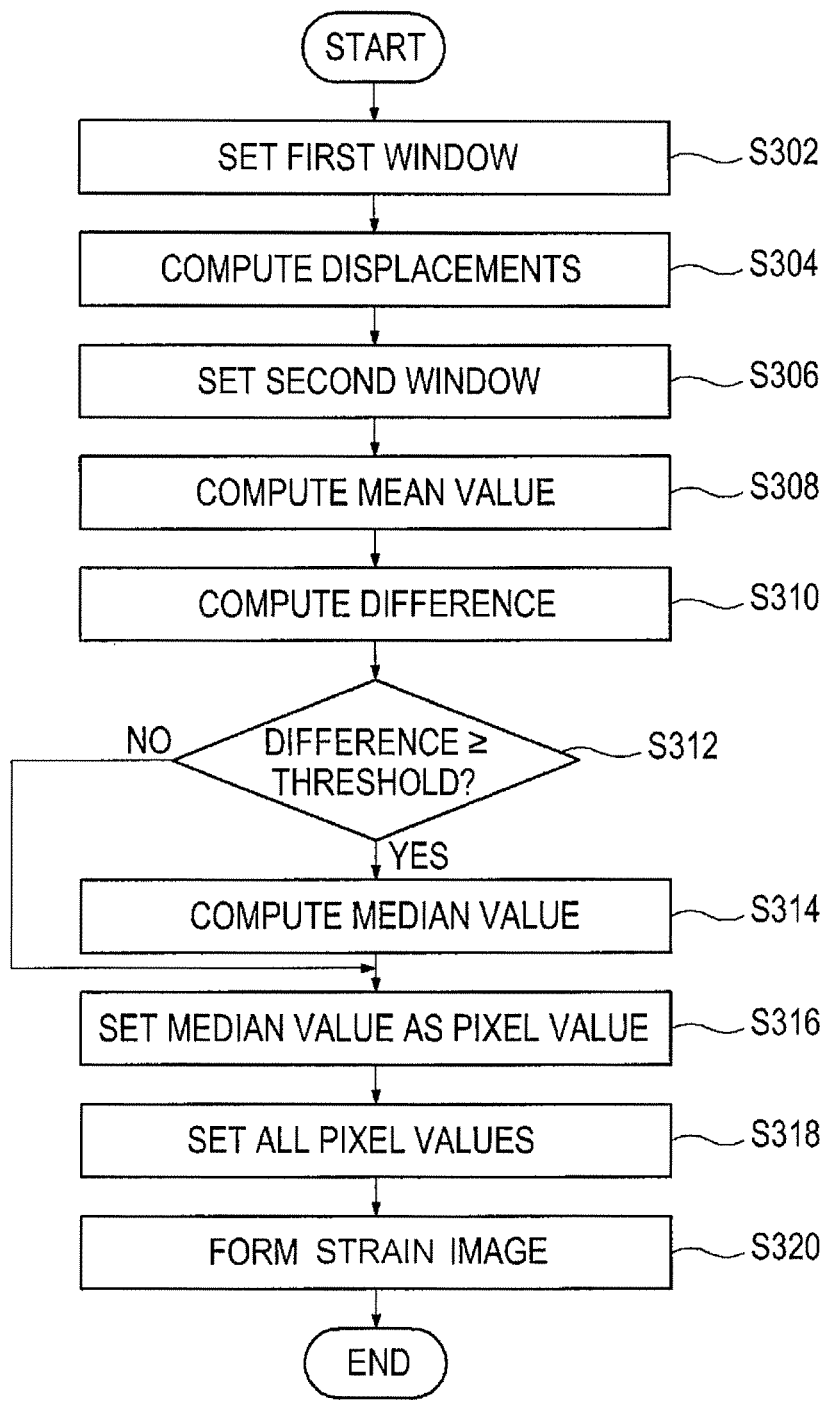
FIG. 3 is a flowchart showing an illustrative embodiment of forming a strain image.

FIG. 3 is a flowchart showing an illustrative embodiment of forming the strain image. Referring to FIG. 3, the processing unit 120 may be configured to set a first window on each of the first ultrasound frame data and the second ultrasound frame data, at S302. The first window may have a predetermined size.

The processing unit 120 may be further configured to move the first window, which has been set on each of the first and second frame data, in a lateral direction by a predetermined interval and compute a correlation between the first and second frame data within the first window to compute a displacement corresponding to each pixel of a $K^{th}$ row $R_K$ (see FIG. 4) in third frame data $F_3$ for an strain image, at S304, wherein K is an integer equal to or greater than 1.

Figure 4:
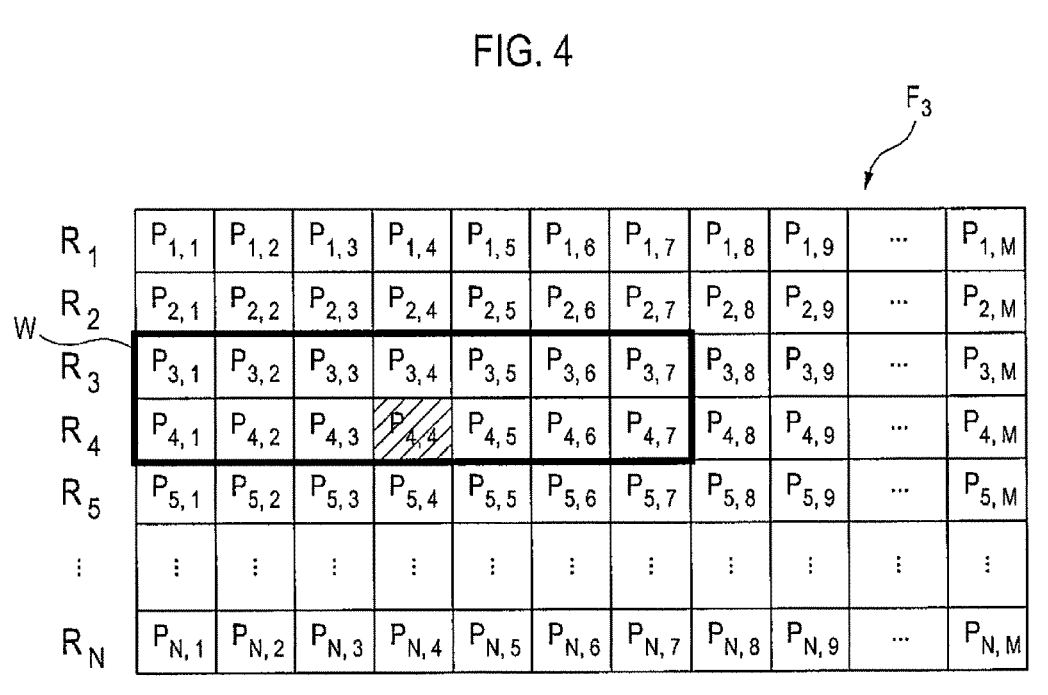

The processing unit 120 may be further configured to set a second window encompassing pixels, which are positioned around one of the pixels of the $K^{th}$ row $R_K$ in the third frame data $F_3$, at S306. As shown in FIG. 4, for example, the processing unit 120 may set a pixel $P_{4,4}$ at a fourth row $R_4$ of the third frame data as a reference pixel and set a second window W to encompass pixels $P_{3,1}$, $P_{3,2}$, $P_{3,3}$, $P_{3,4}$, $P_{3,5}$, $P_{3,6}$ and $P_{3,7}$, which are positioned around the reference pixel, among pixels at a third row $R_3$ and pixels $P_{4,1}$, $P_{4,2}$, $P_{4,3}$, $P_{4,5}$, $P_{4,6}$ and $P_{4,7}$, which are positioned around the reference pixel, among pixels at the fourth row $R_4$.

Although the second window has been described to have a size of 7×2 in the above embodiment, the size of the second window may not be limited thereto. The second window may have various sizes according to necessities.

The processing unit 120 may be further configured to compute an average of pixel values except the reference pixel value within the second window, at S308. As shown in FIG. 4, for example, the processing unit 120 may compute an average of values of pixels $P_{3,1}$, $P_{3,2}$, $P_{3,3}$, $P_{3,4}$, $P_{3,5}$, $P_{3,6}$, $P_{3,7}$, $P_{4,1}$, $P_{4,2}$, $P_{4,3}$, $P_{4,5}$, $P_{4,6}$ and $P_{4,7}$ except the reference pixel $P_{4,4}$ among the pixels $P_{3,1}$, $P_{3,2}$, $P_{3,3}$, $P_{3,4}$, $P_{3,5}$, $P_{3,6}$, $P_{3,7}$, $P_{4,1}$, $P_{4,2}$, $P_{4,3}$, $P_{4,4}$, $P_{4,5}$, $P_{4,6}$ and $P_{4,7}$ within the second window W.

The processing unit 120 may be further configured to compute a difference between the average of pixel values and the reference pixel value (i.e., displacement), at S310, and compare the computed difference with a predetermined threshold, at S312. In this case, the predetermined threshold is a threshold to check whether an error of displacement computation occurs.

If it is determined that the difference is greater than the predetermined threshold, i.e., it is determined that the error of displacement computation occurs, then the processing unit 120 may compute a median value based on the pixel values within the second window, at S314. The processing unit 120 may set the computed median value as a value of the corresponding pixel, at S316. For example, the processing unit 120 may apply a median filter upon the values of the pixels $P_{3,1}$, $P_{3,2}$, $P_{3,3}$, $P_{3,4}$, $P_{3,5}$, $P_{3,6}$, $P_{3,7}$, $P_{4,1}$, $P_{4,2}$, $P_{4,3}$, $P_{4,4}$, $P_{4,5}$, $P_{4,6}$ and $P_{4,7}$ to thereby obtain a median value and set the median value as a value of the pixel $P_{4,4}$ (i.e., substitution).

On the contrary, if it is determined that the difference is less than the predetermined threshold, i.e., it is determined that the error of displacement computation does not occur, then the processing unit 120 may set the displacement computed at S304 as the value of the corresponding pixel.

The processing unit 120 may iteratively perform the above process by moving the first window in an axial direction to thereby set all of values of the pixels of the third frame data, at S318. The processing unit 120 may from a strain image based on the pixel values (i.e., displacements), at S320. The stain image may be formed based on the displacements by using various well-known methods. Thus, a detailed description thereof will be omitted herein.

Referring to FIG. 1, the storage unit 130, which is coupled to the ultrasound data acquisition unit 110 via the processing unit 120, is configured to store the ultrasound frame data acquired in the ultrasound data acquisition unit 110. Also, the storage unit 130 may be configured to store the computed displacements. The display unit 140 may display the strain image, which have been formed in the processing unit 120. The display unit 140 may include at least one of a cathode ray tube (CRT) display, a liquid crystal display (LCD), an organic light emitting diode (OLED) display and the like.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
    an ultrasound data acquisition unit configured to acquire first ultrasound frame data where compression is not applied to a target object and second ultrasound frame data where compression is applied to the target object; and
    a processing unit configured to set a first window on each of the first ultrasound frame data and the second ultrasound frame data, move the first window in a predetermined direction and compute a correlation between the first ultrasound frame data and the second ultrasound frame data within the first window to obtain a displacement corresponding to a value of each pixel of third ultrasound frame data,
    the processing unit being further configured to set one of pixels of the third ultrasound frame data as a reference pixel, set a second window to encompass predetermined numbers of pixels positioned around the reference pixel in the third ultrasound frame data, check whether a displacement computation error corresponding to a dropout occur based on the pixel values within the second window and reset, when the dropout occurs, the value of the reference pixel.

2. The ultrasound system of claim 1, wherein the processing unit is configured to move the first window in a lateral direction and an axial direction.

3. The ultrasound system of claim 1, wherein the processing unit is configured to set the second window to compass the predetermined numbers of the pixels positioned around the reference pixel at a row containing the reference pixel and a previous row.

4. The ultrasound system of claim 1, wherein the processing unit is configured to,
    compute an average of the values of the pixels except the reference pixel with the second window,
    compute a difference between the average and the reference pixel value,
    compare the reference with a threshold predetermined to check whether the displacement computation error occurs,
    compute, when the threshold predetermined occurs, a median values of pixel values with the second window, and
    set the median value as a value of the reference pixel.

5. The ultrasound system of claim 4, wherein the processing unit is configured to apply a median filter to the pixel values within the second window to compute the median value.

6. The ultrasound system of claim 4, wherein the processing unit is configured to set, when the difference is less than the threshold, the displacement as the reference pixel value.

7. A method of correcting a dropout of a strain image in an ultrasound system, comprising:
    a) acquiring first ultrasound frame data where compression is not applied to a target object;
    b) acquiring second ultrasound frame data where compression is applied to the target object;
    c) setting a first window on each of the first ultrasound frame data and the second ultrasound frame data;
    d) moving the first window in a predetermined direction and computing a correlation between the first ultrasound frame data and the second ultrasound frame data within the first window to obtain a displacement corresponding to a value of each pixel of third ultrasound frame data;
    e) setting one of pixels of the third ultrasound frame data as a reference pixel and setting a second window to encompass predetermined numbers of pixels positioned around the reference pixel in the third ultrasound frame data; and
    f) checking whether a displacement computation error corresponding to a dropout occur based on the pixel values within the second window and resetting, when the dropout occurs, the value of the reference pixel.

8. The method of claim 7, wherein the predetermined direction includes a lateral direction and an axial direction.

9. The method of claim 7, wherein the second window is set to compass the predetermined numbers of the pixels positioned around the reference pixel at a row containing the reference pixel and a previous row.

10. The method of claim 7, wherein the step f) includes:
    computing an average of the values of the pixels except the reference pixel with the second window,
    computing a difference between the average and the reference pixel value, comparing the reference with a threshold predetermined to check whether the displacement computation error occurs, computing, when the threshold predetermined occurs, a median values of pixel values with the second window, and setting the median value as a value of the reference pixel.

11. The method of claim 10, wherein a median filter is applied to the pixel values within the second window to compute the median value.

12. The method of claim 10, further comprising setting, when the difference is less than the threshold, the displacement as the reference pixel value.

13. A non-transitory computer-readable storage medium storing instructions that, when executed by a computer, cause the computer to perform a dropout correcting method comprising:

a) setting a first window on each of first ultrasound frame data acquired while compression is not applied to a target object and the second ultrasound frame data acquired while compression is applied to the target object;

b) moving the first window in a predetermined direction and computing a correlation between the first ultrasound frame data and the second ultrasound frame data within the first window to obtain a displacement corresponding to a value of each pixel of third ultrasound frame data;

c) setting one of pixels of the third ultrasound frame data as a reference pixel and setting a second window to encompass predetermined numbers of pixels positioned around the reference pixel in the third ultrasound frame data; and d) checking whether a displacement computation error corresponding to a dropout occur based on the pixel values within the second window and resetting, when the dropout occurs, the value of the reference pixel.

* * * * *